United States Patent [19]

Harrison, Jr.

[11] 4,252,971
[45] Feb. 24, 1981

[54] CHROMATOGRAPHIC PROCESS

[75] Inventor: Roger G. Harrison, Jr., Kalamazoo, Mich.

[73] Assignee: The Upjohn Company, Kalamazoo, Mich.

[21] Appl. No.: 61,682

[22] Filed: Jul. 30, 1979

[51] Int. Cl.$^3$ ............................................. C07H 1/06
[52] U.S. Cl. .................................... 536/17 R; 536/10; 536/12; 536/9
[58] Field of Search ..................... 536/17 R, 10, 12, 9

[56] References Cited

U.S. PATENT DOCUMENTS

| | | | |
|---|---|---|---|
| 3,091,572 | 5/1963 | Luedemann et al. | 536/17 R |
| 3,915,955 | 10/1975 | Cooper et al. | 536/17 R |
| 4,011,390 | 3/1977 | Weinstein et al. | 536/17 R |
| 4,011,391 | 3/1977 | Horii et al. | 536/17 R |
| 4,045,610 | 8/1977 | Nara et al. | 536/17 R |

OTHER PUBLICATIONS

Maehr et al., "Jour. of Chromatography", vol. 30, pp. 572–578, 1967.

*Primary Examiner*—Johnnie R. Brown
*Attorney, Agent, or Firm*—Roman Saliwanchik

[57] ABSTRACT

A chromatographic process for separation of an aminoglycoside antibiotic from impurities. Illustratively, there is disclosed a chromatographic process for separation of the gentamicin complex ($C_1$, $C_2$ and $C_{1a}$) from impurities. The subject process gives a gentamicin complex recovery of more than double the recovery of the best known prior art gentamicin chromatography process.

13 Claims, No Drawings

CHROMATOGRAPHIC PROCESS

BACKGROUND OF THE INVENTION

Aminoglycoside antibiotics are a well-known class of useful antibiotics. Notable among these are gentamicin, neomycin, sisomicin, kanamycin, and the like. The gentamicin fermentation and recovery are disclosed in U.S. Pat. No. 3,091,572. The use of chromatography in a gentamicin recovery process was first described in 1967 by Maehr and Schaffner, "The Separation And Differentiation Of The Gentamicin Complex", J. Chromatog., 30, 572–578. More recently, U.S. Pat. No. 3,915,955 discloses the use of essentially the same chromatography process as described by Maehr and Schaffner, supra.

BRIEF SUMMARY OF THE INVENTION

A solution containing gentamicin and impurities is concentrated to a solids concentration of about 0.5 g/ml, and then subjected to chromatography using a strongly basic ion exchange resin while controlling the pH and temperature of the chromatographic process within certain defined limits. This combination of pH and temperature control gives a surprising improvement of gentamicin recovery of over 100% over the prior art process which does not recognize the criticality of pH and temperature control.

In its broadest scope, the subject invention is a chromatographic process for separation of an aminoglycoside antibiotic from impurities.

DETAILED DESCRIPTION OF THE INVENTION

The invention is described specifically for gentamicin though it can be applied to other aminoglycoside antibiotics.

The gentamicin solution which can be used in the subject process can be obtained from a gentamicin fermentation as disclosed in U.S. Pat. No. 3,091,572. Different methods can be used to process the fermentation beer at harvest to obtain a concentrated aqueous solution containing gentamicin and impurities. In one method described in U.S. Pat. Nos. 3,903,072 and 3,915,955, the beer is filtered at low pH, the filtrate is adjusted to neutral pH with ammonium hydroxide and passed through a bed of weakly acidic cation exchange resin, the resin is washed with water, and the column is eluted with aqueous ammonium hydroxide. The eluate is then concentrated. Another method is to screen the beer, pass the screened beer at neutral pH over a mixed weakly acidic cation exchange resin (using the methodology disclosed in U.S. Pat. No. 2,786,831), wash the resin with water, and then elute and concentrate as in the first method described above.

At the start of each chromatography the resin bed is brought to the desired temperature by adjusting the temperature of water flowing through the jacket of the column. The concentrated eluate feed, prepared as described above, is charged to the top of the column and is slowly lowered into the resin bed until the liquid level is just below the top of the resin bed. Then water at the operating temperature is pumped downflow through the column at a rate to give a 34 minute residence time. A void fraction of 0.35 is assumed in calculating the flow rate from the residence time. In every chromatography at least 1.5 bed volumes of water eluant are used.

An automatic fraction collector is used to obtain eluate fractions. Typically, a 0.25 bed volume precut is taken followed by 0.035 bed volume fractions until the end of the elution.

Thin layer chromatography (tlc) is performed on chromatography fractions using the following procedure.

1. Spot 20 μl of eluate on a silica gel plate (E. Merck Silica Gel 60 F-254 plate). Also spot 20 μl of a control containing 10 mg/ml of gentamicin sulfate.
2. Place the plate in a chromatographic chamber containing the lower layer of a mixture of methanol-chloroform-concentrated ammonium hydroxide (1:1:1).
3. Develop the plate to a height of 15 cm (takes about 2 hours).
4. Dry the plate with hot air, spray with ninhydrin (E. Merck Ninhydrin Spray Reagent 0.1%), and heat on a hot plate until dark spots appear.

The preferred conditions for the subject chromatography process begin with the solids concentration of the gentamicin feed concentrate. A solids concentration of about 0.5 g/ml is preferred. A lower concentration results in a wider feed band in the chromatography column which then leads to poorer separation.

The pH of the feed can vary from about 3.0 to about 11.0. A feed pH of about 7.0 is preferred The chromatography column is prepared with a strongly basic ion exchange resin, for example, Dowex 1-X2 (Dow Chem.), Amberlite IRA-401S (Rohm and Haas), and Duolite A-143 (Diamond Shamrock). Dowex 1-X2 is the preferred resin.

The ratio of resin volume to gentamicin bioactivity in the feed is not critical. A resin volume of about 140 ml of resin per gram of gentamicin bioactivity in the feed concentrate is preferred. As this ratio is lowered, the resolution of gentamicin from impurities will be less favorable.

It is preferred that the resin be in the hydroxide form for good results. For example, the sulfate form gives good recovery but relatively poor separation of gentamicin from impurities.

The temperature of the resin bed and of the water elutant, as well as the pH of the feed, are critical. An increase in temperature above room temperature, i.e. about 25° to about 100° C., gives increased gentamicin recovery in the chromatography eluate. As the feed pH is increased, the temperature must be increased to give equivalent gentamicin recovery. Temperatures and pH's which are preferred are about 60° C. at about pH 5.0, about 70° C. at about pH 7.0, and, about 75° C. at about pH 9.0.

The residence time of the feed in the column is not critical. Thus, the residence time can vary from about 10 minutes to about 300 minutes. A residence time of about 34 minutes is preferred.

The following is illustrative of the preferred embodiments of the claimed process. It represents the best mode for performing the process. As stated above, the allowable parameters extend beyond these preferred conditions, and, therefore, the following should not be construed as limiting the scope of the invention process. All percentages are by weight and all solvent mixture proportions are by volume unless otherwise noted.

A. Concentrate a solution containing gentamicin and impurities to a solids concentration of 0.2 g/ml. Adjust the pH to 7.0 with 18 N sulfuric acid. Concentrate further to a solids concentration of 0.5 g/ml.

B. To a column, add 140 ml of Dowex 1-X2 strongly basic ion exchange resin (hydroxide form; 16–100 mesh) per gram of gentamicin bioactivity in the feed concentrate in Step A.

C. Heat the bed of resin to 70° C.

D. Charge the feed concentrate to the top of the resin bed and slowly lower into the resin bed until the liquid level is just below the top of the bed.

E. Pump 1.5 bed volumes of water (deionized is preferred) at 70° C. downflow through the column at a rate to give a 34 minute residence time in the column.

F. Initially collect a 0.25 bed volume fraction of the column effluent and then obtain 0.035 bed volume fractions.

G. Analyze the fractions for gentamicin and impurities by tlc. Pool the gentamicin-rich fractions.

Following is a tabulation of the data obtained on four runs using the above process conditions:

| Dowex 1-X2 Chromatographies pH 7.0 Feed And 70° C. | | | | |
|---|---|---|---|---|
| | | Recovery of Bioactivity | | Purity |
| Run | Column Diameter × Height, Inches | Total Eluate, % | Rich Eluate, % | Feed, % | Rich Eluate, % |
| 1 | 4 × 48 | 98 | 78 | 61 | 72 |
| 2 | 14 × 126 | 88 | 81 | 57 | 88 |
| 3 | 14 × 92 | 105 | 97 | 65 | 93 |
| 4 | 14 × 92 | 109 | 100 | 47 | 88 |
| | Average | 100 | 89 | 58 | 85 |

| Hplc Data For Pilot Plant Chromatographies pH 7.0 Feed And 70° C. | | | | | | |
|---|---|---|---|---|---|---|
| | Feed | | | Rich Eluate | | |
| Run | % $C_1$ | % $C_2$ | % $C_{1a}$ | % $C_1$ | % $C_2$ | % $C_{1a}$ |
| 1 | 29 | 37 | 34 | 29 | 36 | 35 |
| 2 | 36 | 46 | 18 | 37 | 47 | 16 |
| 3 | 28 | 41 | 31 | 28 | 42 | 30 |
| 4 | 29 | 43 | 28 | 29 | 44 | 27 |

Note:
$C_1$, $C_2$, and $C_{1a}$ are the major components of the gentamicin complex discussed herein. Hplc (high pressure liquid chromatography) is a standard test, see J. Anhalt, F. C. Sancilio and T. McCorkle, "Gentamicin-C-Component Ratio Determination by High Pressure Liquid Chromatography", J. Chromatog., 153, 489–493 (1978).

The gentamicin bioactivity in solutions is determined by use of a standard turbidimetric assay using *S. aureus*.

I claim:

1. An ion exclusion chromatographic process for separation of an aminoglycoside antibiotic from impurities which comprises controlling the pH of the antibiotic feed solution at about 3 to about 11, and controlling the temperature of the strongly basic anion exchange resin in the chromatographic column at about 25° to 100° C.

2. A process, according to claim 1, wherein the pH of the aminoglycoside antibiotic feed solution is controlled at about 5.0 and the temperature of the chromatographic column is controlled at about 60° C.

3. A process, according to claim 1, wherein the pH of the aminoglycoside antibiotic feed solution is controlled at about 7.0 and the temperature of the chromatographic column is controlled at about 70° C.

4. A process, according to claim 1, wherein the pH of the aminoglycoside antibiotic feed solution is controlled at about 9.0 and the temperature of the chromatographic column is controlled at about 75° C.

5. A process, according to claim 1, wherein the aminoglycoside antibiotic is the gentamicin complex and the antibiotic feed solution is gentamicin feed solution.

6. A process, according to claim 5, wherein the pH of the gentamicin feed solution is controlled at about 3 to about 11 and the temperature of the chromatographic column is controlled at about 25° to about 100° C.

7. A process, according to claim 6, wherein the pH of the gentamicin feed solution is controlled at about 7.0 and the temperature of the chromatographic column is controlled at about 70° C.

8. A process, according to claim 6, wherein the pH of the gentamicin feed solution is controlled at about 9.0 and the temperature of the chromatographic column is controlled at about 75° C.

9. A chromatographic process for separation of an aminoglycoside antibiotic from impurities which comprises:
(a) adjusting the pH of an aminoglycoside antibiotic solution from about 3.0 to about 11.0;
(b) passing said pH adjusted solution over a strongly basic ion exchange resin which has been heated to a temperature in the range of 25° to 100° C.;
(c) passing water at a temperature in the range of 25° to 100° C. through the chromatographic column; and,
(d) collecting aminoglycoside antibiotic-rich fractions.

10. A process, according to claim 9, wherein said aminoglycoside antibiotic is the gentamicin complex, the aminoglycoside antibiotic solution in step (a) is a gentamicin concentrate, and, the aminoglycoside antibiotic-rich fractions are gentamicin-rich fractions.

11. A process, according to claim 9, wherein the pH of the aminoglycoside antibiotic solution is adjusted to about 7.0 and the temperature of the chromatographic column is controlled at about 70° C.

12. A process, according to claim 9, wherein said strongly basic ion exchange resin is in the hydroxide form.

13. A process, according to claim 9, wherein the strongly basic ion exchange resin is Dowex 1-X2 in the hydroxide form.

* * * * *